(12) United States Patent
Steif

(10) Patent No.: US 10,722,383 B2
(45) Date of Patent: Jul. 28, 2020

(54) FEMORAL HEAD PRESS INSTRUMENT FOR PROSTHETIC IMPLANT

(71) Applicant: Zimmer, Inc., Warsaw, IN (US)

(72) Inventor: Matthew Steif, Mishawaka, IN (US)

(73) Assignee: Zimmer, Inc., Warsaw, IN (US)

( * ) Notice: Subject to any disclaimer, the term of this patent is extended or adjusted under 35 U.S.C. 154(b) by 318 days.

(21) Appl. No.: 15/592,309

(22) Filed: May 11, 2017

(65) Prior Publication Data

US 2017/0325972 A1 Nov. 16, 2017

Related U.S. Application Data

(60) Provisional application No. 62/334,519, filed on May 11, 2016.

(51) Int. Cl.
| | |
|---|---|
| *A61B 17/58* | (2006.01) |
| *A61B 17/88* | (2006.01) |
| *A61F 2/46* | (2006.01) |
| *A61F 2/36* | (2006.01) |
| *A61F 2/30* | (2006.01) |

(52) U.S. Cl.
CPC .......... *A61F 2/4637* (2013.01); *A61F 2/3609* (2013.01); *A61F 2002/30523* (2013.01); *A61F 2002/365* (2013.01); *A61F 2002/4681* (2013.01)

(58) Field of Classification Search
CPC ........ A61F 2/46; A61F 2/4607; A61F 2/4637; A61F 2/3609; A61F 2002/365; A61F 2002/4681; A61F 2002/30523
USPC ................ 606/99–100, 89; 623/23.11–23.38
See application file for complete search history.

(56) References Cited

U.S. PATENT DOCUMENTS

| | | | |
|---|---|---|---|
| 5,015,257 A | 5/1991 | Crowninshield et al. | |
| 5,133,765 A | 7/1992 | Cuilleron | |
| 5,849,015 A * | 12/1998 | Haywood | A61F 2/4607 606/99 |
| 6,974,483 B2 | 12/2005 | Murray | |
| 8,123,754 B2 | 2/2012 | Siebel et al. | |
| 8,562,690 B1 | 10/2013 | Dickerson | |
| 8,628,577 B1 * | 1/2014 | Jimenez | A61F 2/447 623/17.15 |
| 2003/0229357 A1 | 12/2003 | Dye | |

(Continued)

OTHER PUBLICATIONS

"Modular Bipolar Femoral Head Replacement", Zimmer—Surgical Technique, (May 30, 2015), 12 pgs.

*Primary Examiner* — Jessica Weiss
(74) *Attorney, Agent, or Firm* — Schwegman Lundberg & Woessner, P.A.

(57) ABSTRACT

A femoral head press can comprise: a frame having first end second ends; a clamp connected to the first end to define a holding plane; a mechanical drive mechanism mounted to the second end and having a drive axis; a ram connected to the second end; and a femoral head cup connected to the ram; wherein the mechanical drive mechanism is configured to drive the ram along the drive axis substantially perpendicular to the holding plane to advance the femoral head cup toward the clamp. A method for assembly a femoral head to a stem neck can comprise: attaching a clamp of a frame of a femoral head press to a neck of a femoral stem; connecting a femoral head to a cup connected to a ram slidably engaged with the frame; and actuating a mechanical drive mechanism coupled to the frame to advance the cup toward the neck.

19 Claims, 6 Drawing Sheets

(56) References Cited

U.S. PATENT DOCUMENTS

| | | | |
|---|---|---|---|
| 2008/0167723 A1 | 7/2008 | Acker et al. | |
| 2010/0152742 A1 | 6/2010 | Nevelos et al. | |
| 2010/0298834 A1* | 11/2010 | Hildebrandt | A61B 17/025 606/80 |
| 2011/0004318 A1* | 1/2011 | Tulkis | A61B 17/1668 623/23.11 |
| 2011/0071534 A1* | 3/2011 | Tuke | A61F 2/4607 606/89 |
| 2013/0053966 A1* | 2/2013 | Jimenez | A61F 2/4611 623/17.16 |
| 2016/0206430 A1* | 7/2016 | Grostefon | A61F 2/3094 623/22.11 |
| 2016/0206433 A1* | 7/2016 | Grostefon | A61F 2/3607 623/22.11 |
| 2017/0196711 A1* | 7/2017 | Behzadi | A61F 2/4609 623/22.11 |
| 2018/0092757 A1* | 4/2018 | Behzadi | A61F 2/3609 623/22.11 |

* cited by examiner

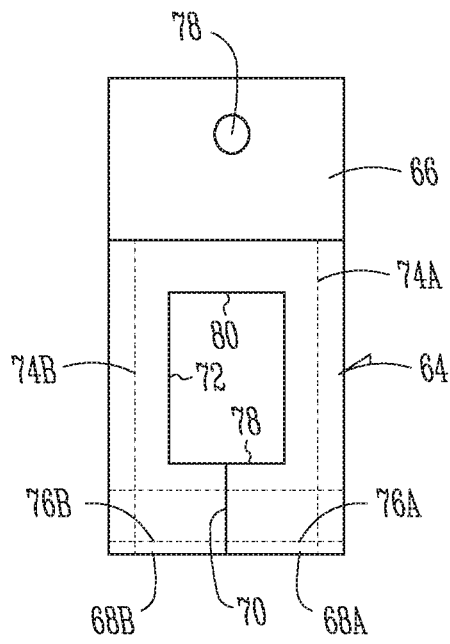
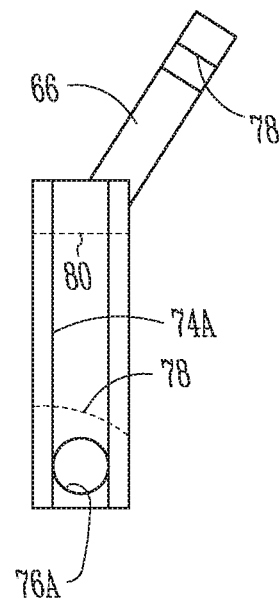
Fig.2A      Fig.2B
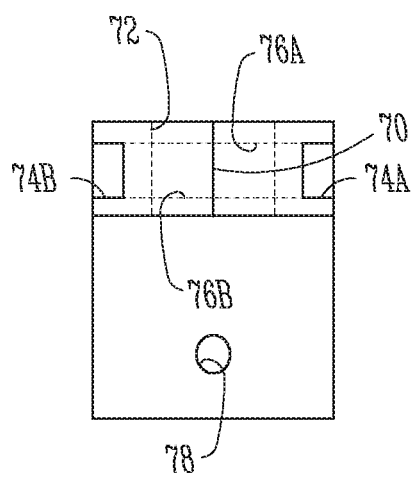
Fig.2C

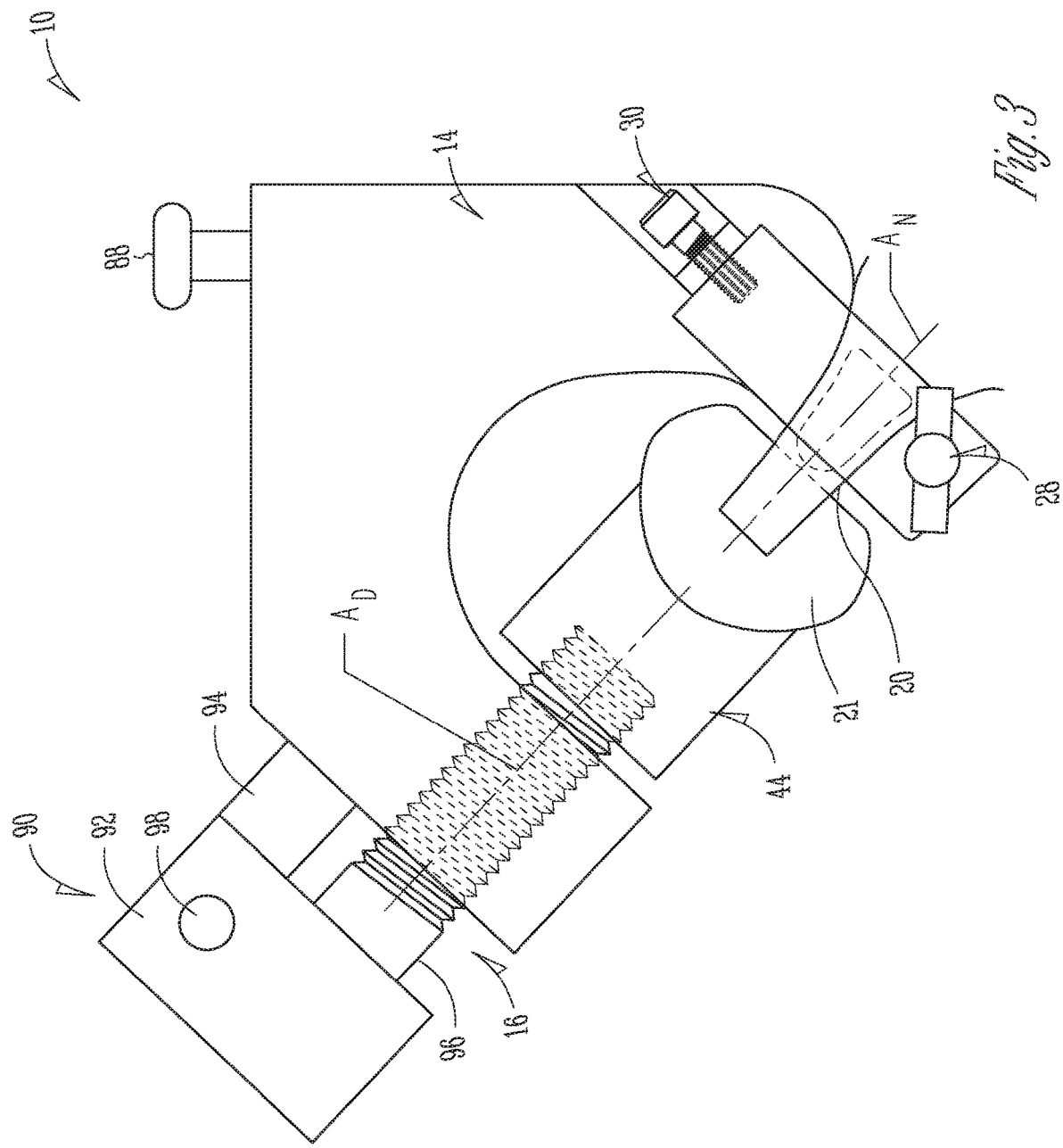

FEMORAL HEAD PRESS INSTRUMENT FOR PROSTHETIC IMPLANT

CLAIM OF PRIORITY

This application claims the benefit of U.S. Provisional Patent Application Ser. No. 62/334,519, filed on May 11, 2016, the benefit of priority of which is claimed hereby, and which is incorporated by reference herein in its entirety.

TECHNICAL FIELD

This document pertains generally, but not by way of limitation, to surgical instruments for implanting prosthetic devices. More particularly, this disclosure relates to, but not by way of limitation, instruments for aligning and assembling components of a prosthetic device.

BACKGROUND

Surgery to replace the femoral portion of a hip joint in total joint surgery can involve the insertion of a stem in a cavity formed in the femur. The end of the stem extending from the cavity has a neck which is formed at an angle, and a ball disposed on the neck is mated with a socket in the hip. Patients can require individual fitting of the implant due to the unique anatomical requirements of each particular patient. Some prosthetic implants can be unitary in nature, wherein the femoral stem and the ball are made from the same component. However, such unitary devices can require the hospital or surgeon to have a large quantity of prostheses available in order to be able to provide a correct fit for each patient. It can be very costly to maintain a large inventory of unitary prostheses. Furthermore, despite having a large number of unitary prostheses to choose from, an optimally fitting prosthetic cannot always be found. This leaves the surgeon to use the best fitting prosthetic available, which may result in discomfort for the patient.

More recently, modular prostheses have been designed to overcome this longstanding problem. Exemplary modular prostheses are described in U.S. Pat. No. 5,015,257 to Crowninshield et al., U.S. Pat. No. 8,562,690 to Dickerson, and U.S. Pub. No. 2008/0167723 to Acker et al. These prostheses, however, can result in the surgeon needing to intraoperatively align and connect various components. Typically, a surgeon is left to manually assemble the various components using different holding devices and a mallet or hammer to apply the desired assembly force. Due to differences between surgeons and each particular patient, these procedures can result in considerable variation in the final implanted prosthetic. Such procedures are described in U.S. Pat. No. 6,974,483 to Murray and U.S. Pub. No. 2003/0229357 to Dye.

Examples of various surgical instruments are described in U.S. Pat. No. 5,133,765 to Cuilleron, U.S. Pat. No. 8,123,754 to Siebel et al., U.S. Pub. No. 2010/0152742 to Nevelos et al., U.S. Pub. No. 2011/0004318 to Tulkis et al., and U.S. Pub. No. 2011/0071534 to Tuke.

OVERVIEW

The present inventors have recognized, among other things, that a problem to be solved can include the need for surgeons to have to manually align one prosthetic component with another and subsequently, while maintaining alignment, impact one of the components to mechanically couple the components together. This situation can be particularly difficult in the context of assembling a femoral head or ball onto a femoral stem neck. The present inventors have recognized that the force delivered by various surgeons can widely vary and may not reach a desired force to correctly seat the ball on the neck. The present inventors have recognized that improperly impacted femoral heads can result in fretting corrosion in vivo, which may produce deleterious results, such as patient pain, adverse tissue reactions, pseudo tumors and the like.

The present subject matter can help provide a solution to this problem, such as by providing the surgeon with a surgical instrument that aligns the femoral head with the neck, and that utilizes a mechanical advantage to assemble the head onto the neck in the desired orientation and with the desired force, thereby inhibiting or preventing fretting corrosion and other deleterious results.

A femoral head press can comprise: a frame having a first end and a second end; a clamp connected to the first end of the frame, the clamp defining a holding plane; a mechanical drive mechanism mounted to the second end of the frame, the mechanical drive mechanism having a drive axis; a ram connected to the second end of the frame; and a femoral head cup connected to the ram; wherein the mechanical drive mechanism is configured to drive the ram along the drive axis substantially perpendicular to the holding plane to advance the femoral head cup toward the clamp.

A method for assembly a femoral head to a stem neck of a prosthetic device can comprise: attaching a clamp of a frame of a femoral head press to a neck of a femoral stem; connecting a femoral head to a cup connected to a ram slidably engaged with the frame; and actuating a mechanical drive mechanism coupled to the frame to advance the ram and cup toward the neck.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

FIGS. 2A-2C are top, side and front views of the insert of FIG. 1C.

FIG. 3 is a side schematic view of the femoral head press of FIG. 1A having a motor attached to the threaded ram.

Figure 1A:
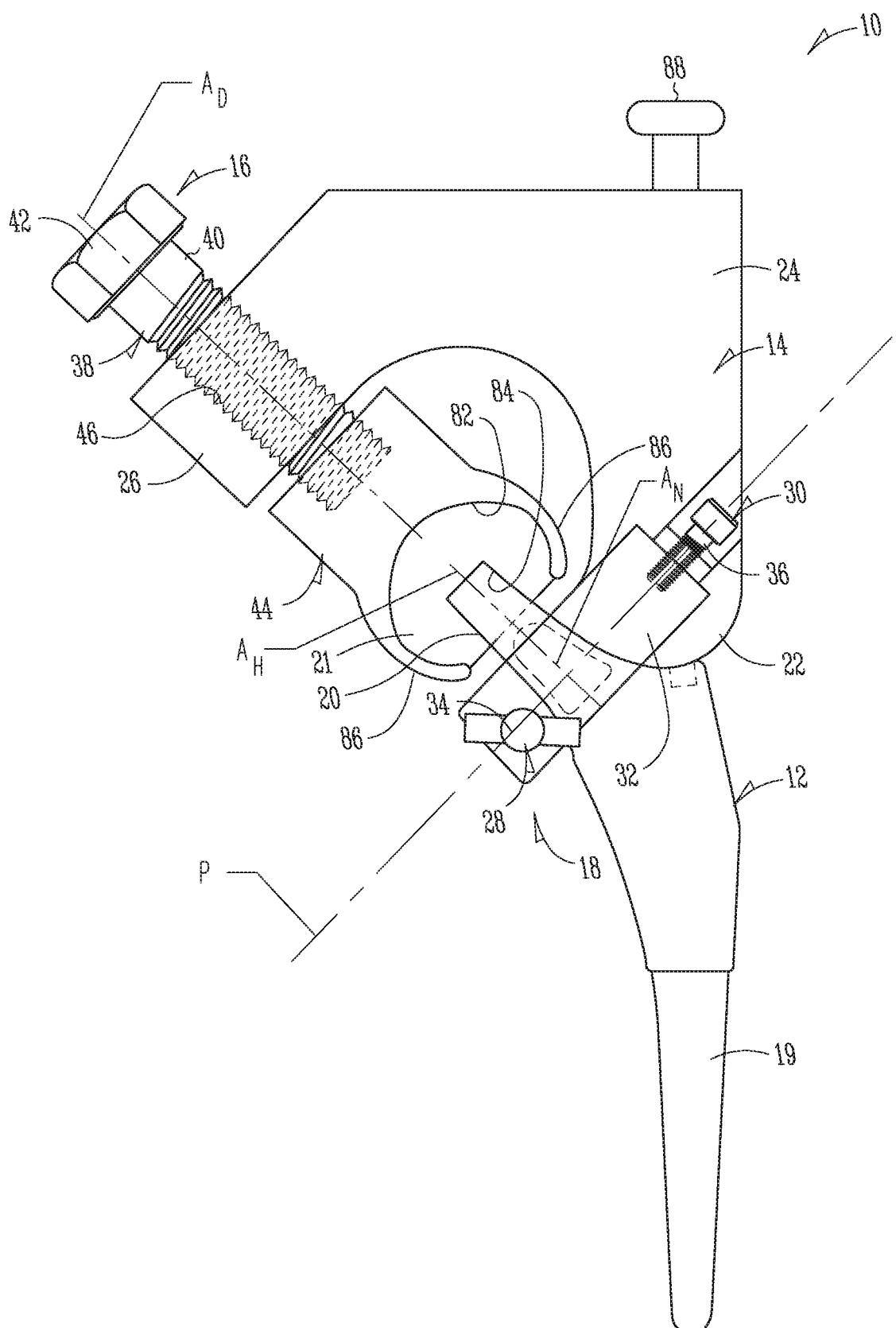
FIG. 1A is a side schematic view of a femoral head press having a frame that attaches to a stem neck and a mechanical press comprising a threaded ram.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

FIG. 1A is a side schematic view of femoral head press 10 connected to prosthetic stem 12. Femoral head press 10 can include frame 14, mechanical press 16 and clamp mechanism 18. Prosthetic stem 12 can include shank 19, neck 20 and head 21. Shank 19 of stem 12 can be inserted into cancellous bone of a femur (not shown) in a manner so that neck 20 extends from a resected proximal end of the femur when the natural or anatomic femoral head is removed. Neck 20 can extend from shank 19 along neck axis $A_N$. Head 21 can be a separate component that can be assembled to neck 20 with the use of femoral head press 10.

Frame 14 can comprise a rigid body that can fixedly support mechanical press 16 relative to clamp mechanism 18. In various examples, frame 14 can be fabricated from a stainless steel, such as 417 stainless steel. Support end 22 of frame 14 can extend in a plane generally (e.g., within +/− five degrees) perpendicular to axis $A_N$. Bridge portion 24 of frame 14 can extend away from support end 22 to position drive end 26 opposite support end 22. Drive end 26 can extend in a plane generally (e.g., within +/− five degrees) perpendicular to drive axis $A_D$. As such, rigidity provided by frame 14 can help ensure that drive axis $A_D$ of mechanical press 16 aligns with clamp mechanism 18 and neck axis $A_N$ to facilitate assembly of head 21 to neck 20.

Support end 22 of frame 14 can be connected to neck 20 via clamp mechanism 18. Clamp mechanism 18 can include locking device 28 and tensioning device 30. Clamp mechanism 18 can comprise clamp or collar 32 that can allow support end 22 of frame 14 to open to accept neck 20, as discussed below with reference to FIG. 1B. Collar 32 can be disposed in a plane substantially (e.g., within +/− five degrees) parallel to holding plane P. Locking device 28 can include fastener 34 that allows collar 32 to be tightly closed around neck 20. Similarly, tensioning device 30 can include fastener 36 that facilitates insert 50 (FIGS. 2A-2C) being centered along axis $A_N$ and tightening of insert 50 on neck 20.

Mechanical press 16 of frame 14 can be connected to drive end 26 of frame 14. In the embodiment of FIG. 1A, mechanical press 16 comprises ram 38, which can comprise shaft 40, knob 42 and cup 44. Drive end 26 of frame 14 can include bore 46 that can be configured to receive shaft 40. In an example, shaft 40 and bore 46 can include mating threads that allow ram 38 to be advanced and retreated along drive axis $A_D$. In an example, the threads can be box threads that facilitate easy torque transmission between shaft 40 and bore 46. Knob 42 can be attached to a proximal end of shaft 40 to facilitate rotation of shaft 40. In an example, knob 42 can be a hex head to allow knob 42 to mate with a wrench. In various examples, ram 38 can be fabricated from a stainless steel, such as 304 stainless steel. Cup 44 can be attached to a distal end of shaft 40 to facilitate coupling with femoral head 21.

Figure 1B:
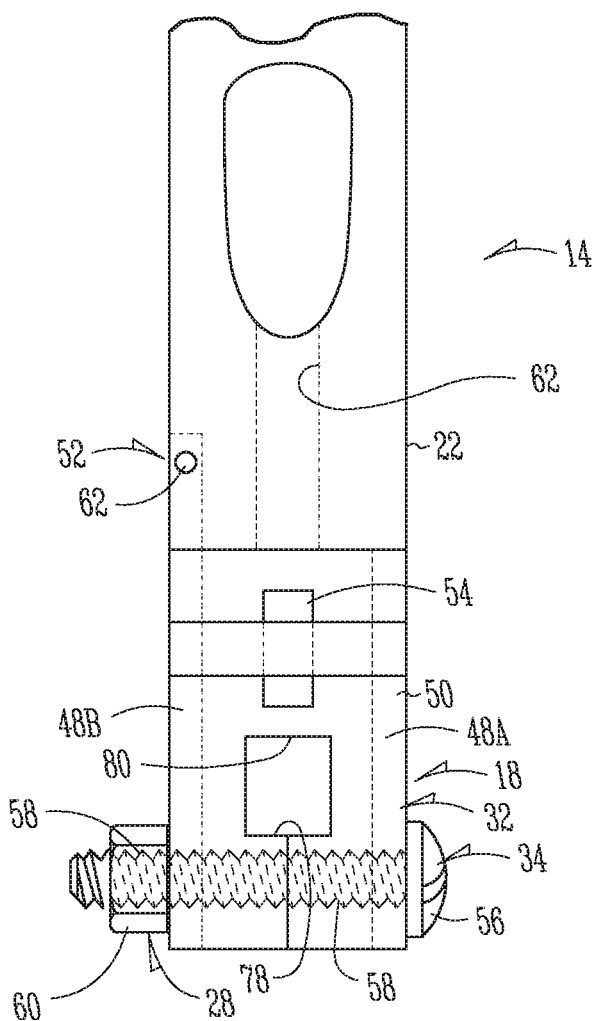
FIG. 1B is a broken away bottom view of the femoral head press of FIG. 1A showing a clamp mechanism attaching the frame to the stem neck.
Figure 1C:
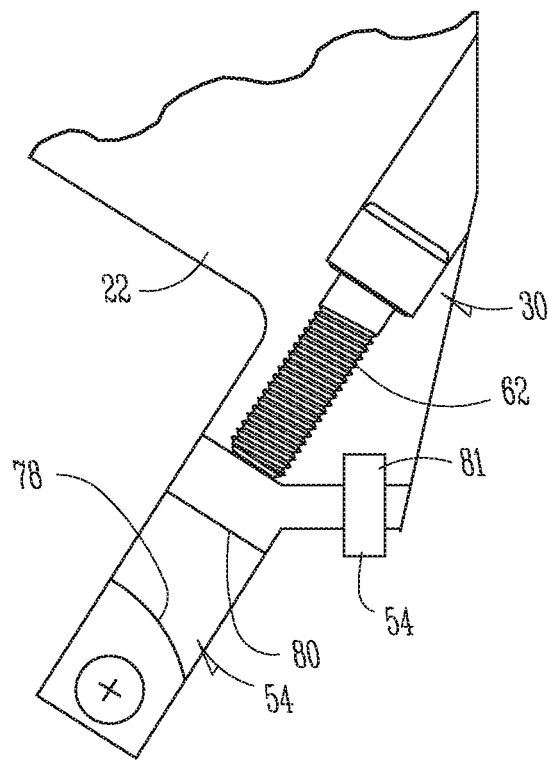
FIG. 1C is a side cross-sectional view of the clamp mechanism of FIG. 1B showing an insert providing a buffer between the clamp mechanism and the stem neck.

FIG. 1B is a broken away bottom view of femoral head press 10 of FIG. 1A showing clamp mechanism 18 attaching frame 14 to stem neck 20. FIG. 1C is a side cross-sectional view of clamp mechanism 18 of FIG. 1B showing insert 50 providing a buffer between clamp mechanism 18 and stem neck 20.

Frame 14 can include support end 22 extending from bridge portion 24 (FIG. 1A). Clamp mechanism 18 can include locking device 28 and collar 32. Collar 32 can include jaws 48A and 48B, and insert 50. Jaw 48A can be integral with support end 22 and jaw 48B can be connected to support end 22 with a fastener at pivot 52. Insert 50 can be connected to support end 22 via a fastener, such as pin 54. Clamp mechanism 18 can include fastener 34, head 56, shank 58 and nut 60. Nut 60 can be removed from shank 58 of fastener 34 in order to allow jaw 48B to be rotated away from support end 22 at pivot 52 on pin 62. With jaw 48B rotated away, insert 50 and stem 12 can be positioned within collar 32. Insert 50 can be coupled to support end 22 via pin 54 and can be snapped into engagement with jaws 48A and 48B.

FIGS. 2A-2C are top, side and front views of insert 50 of FIG. 1C. Insert 50 can include collet portion 64 and extension portion 66. Collet portion 64 can include first arm 68A, second arm 68B, split 70, socket 72, first channel 74A, second channel 74B and aligned bores 76A and 76B. Extension portion 66 can include bore 78.

Socket 72 can be shaped to engage neck 20. Socket 72 can have different shapes for different implants to be assembled with press 10. Thus, in one example, forward surface 78 can be curved while rear surface 80 can be flat. Split 70 can be included in collet portion 64 to facilitate assembly of insert 50 with neck 20. Insert 50 can be made of a resilient material to engage with neck 20. In various examples, insert 50 can be made of nylon, silicon, Raydel® or the like. Insert 50 protects neck 20 against damage from clamp 32 and also facilitates aligning of neck 20 with shaft 40. Additionally, insert 50 allows femoral head press 10 to be used with a variety of different prosthetic implants. For example, the interior surfaces of insert 50 that form socket 72, such as forward surface 78 and rear surface 80, can be shaped differently for different implants, while the exterior surfaces, such as those forming channels 74A and 74B, can be the same for every implant.

The back of insert 50 can engage support end 22 using extension portion 66. Specifically, extension portion 66 can be angled out from collet portion 64 to lie flush against support end 22. Pin 54 can be inserted through bore 78 and into bore 81 in support end 22 to hold extension portion 66 in place. Extension portion 66 and pin 54 can be configured to simultaneously engage stem 12. For example, extension portion 66 can be sandwiched between a surface of stem 12 and support end 22, with pin 54 extending through extension portion 66 and into both bore 81 and bore 83 (FIG. 1A) of stem 12.

The sides of insert 50 can engage support end 22 using channels 74A and 74B. Specifically, arms 68A and 68B can include channels 74A and 74B, respectively, to engage with jaws 48A and 48B of collar 32, thereby capturing insert 50 within collar 32. Channels 74A and 74B and jaws 48A and 48B can be sized and shaped to provide an interference fit that snaps and holds insert 50 into place on support end 22.

The front of insert 50 can engage support end 22 of frame 14 using aligned bores 76A and 76B. Specifically, arms 68A and 68B can also include aligned bores 78A and 78B to receive shaft 58 of fastener 34. In other examples, arms 68A and 68B can include front end flanges that extend from arms 68A and 68B toward each other to further retain insert 50.

Thus, inset 50 can be positioned in collar 32 so that jaws 48A and 48B engage channels 74A and 74B, respectively. Jaw 48B can be rotated back into engagement with insert 50 and shaft 58 can be inserted into bores in jaws 48A and 48B and aligned bores 76A and 76B. Nut 60 can be threaded onto shaft 58 to tighten insert 50 into place. Insertion of pin 54 into bore 78 and aligned bore 81 in support end 22 can hold insert 50 in place.

As can be seen in FIG. 1C, fastener 36 of tensioning device 30 can be threaded into bore 62 in support end 22. Bore 62 and fastener 36 can have mating threads that allow fastener 36 to push against insert 50. Thus, with fastener 34 and pin 54 in place, and neck 20 inserted into socket 72, fastener 36 can be advanced to push neck 20 into alignment with shaft 40. In particular, positioning of insert 50 by fastener 36 can help align neck axis $A_N$ with drive axis $A_D$. Also, because insert 50 can be soft and resilient, neck 20 can remain unblemished and undamaged. Insert 50 can be plastically deformed during use and can thus, in some embodiments, be a one-time use, disposable component.

After press 10 has been assembled to stem 12, femoral head 21 can be connected to cup 44. Cup 44 can include cavity 82 that conforms to the outer surface of head 21. Cup 44 can thus be shaped so that head 21 fits within cavity 82 in only one way so that socket 84 is centered on drive axis $A_D$. In other words, head axis AH can align with drive axis $A_D$ when head 21 is properly seated in cup 44. Different sized cups can be mounted to shaft 40 for use with different sized heads. Thus, cup 44 can be connected to shaft 40 using means that allow for repeated, releasable engagement, such as a threaded connection. In an example, cup 44 can also include fingers 86 that can flex to allow head 21 to be inserted in cavity 82, but that grab onto head 21 to hold head 21 in only one orientation. For example, fingers 86 can engage a flat bottom surface of head 21 that faces towards collar 32.

Next, mechanical press 16 can be operated to advance shaft 40 toward collar 32. In one example, femoral head press 10 can be manually operated and supported, e.g., manually held and manipulated. Knob 42 can be manually rotated or a tool can be attached to knob 32 to facilitate rotation of shaft 40. For example, knob 42 can be a hex head to engage a correspondingly sized wrench. Handle 88 can also be grasped in order to gain leverage in rotating shaft 40 and to facilitate balancing of frame 14 relative to stem 12. Because drive axis $A_D$ is aligned with neck axis $A_N$, head 21 can be advanced properly into position on neck 20. In another example, femoral head press can be supported by a stand that positions femoral head press 10 relative to the anatomy of the patient and then subsequently manually operated. However, as discussed below, various femoral head presses of the present disclosure can be operated under external power.

FIG. 3 is a side schematic view of femoral head press 10 of FIG. 1A having motor 90 attached to mechanical press 16. Femoral head press 10 of FIG. 3 includes the same components as those shown and described with reference to FIG. 1A. However, motor 90 can be attached to frame 14 in order to automate the rotation of shaft 40. Motor 90 can include housing 92, which can be coupled to frame 14 via mounting bracket 94. Mounting bracket 94 can be connected to housing 92 and frame 14 by any suitable means, such as fasteners, welding or the like. Motor 90 can also include drive shaft 96, which can be connected to shaft 40 via any suitable means. For example, drive shaft 96 can be directly welded to shaft 40 as shown in FIG. 3 such that knob 42 can be omitted. In other examples, drive shaft 96 can coupled to knob 42 via a socket (not shown) or some other mechanical interaction. Motor 90 can include activation button 98 that can be depressed to commence rotation of drive shaft 96. Motor 90 can be activated by any suitable power source. For example, motor 90 can be an electric motor or a pneumatic motor. Motor 90 can be powered by an internal power source, such as a battery, or an external power source, such as a power cord connected to an electrical outlet or an air hose connected to a source of compressed air. Motor 90 can allow a surgeon or operator of femoral head press 10 to automatically and precisely control placement of head 21. Thus, the surgeon can concentrate on monitoring engagement of head 21 with stem 20 and the rest of the surgical procedure, rather than being distracted by operation of mechanical press 16.

Figure 4:
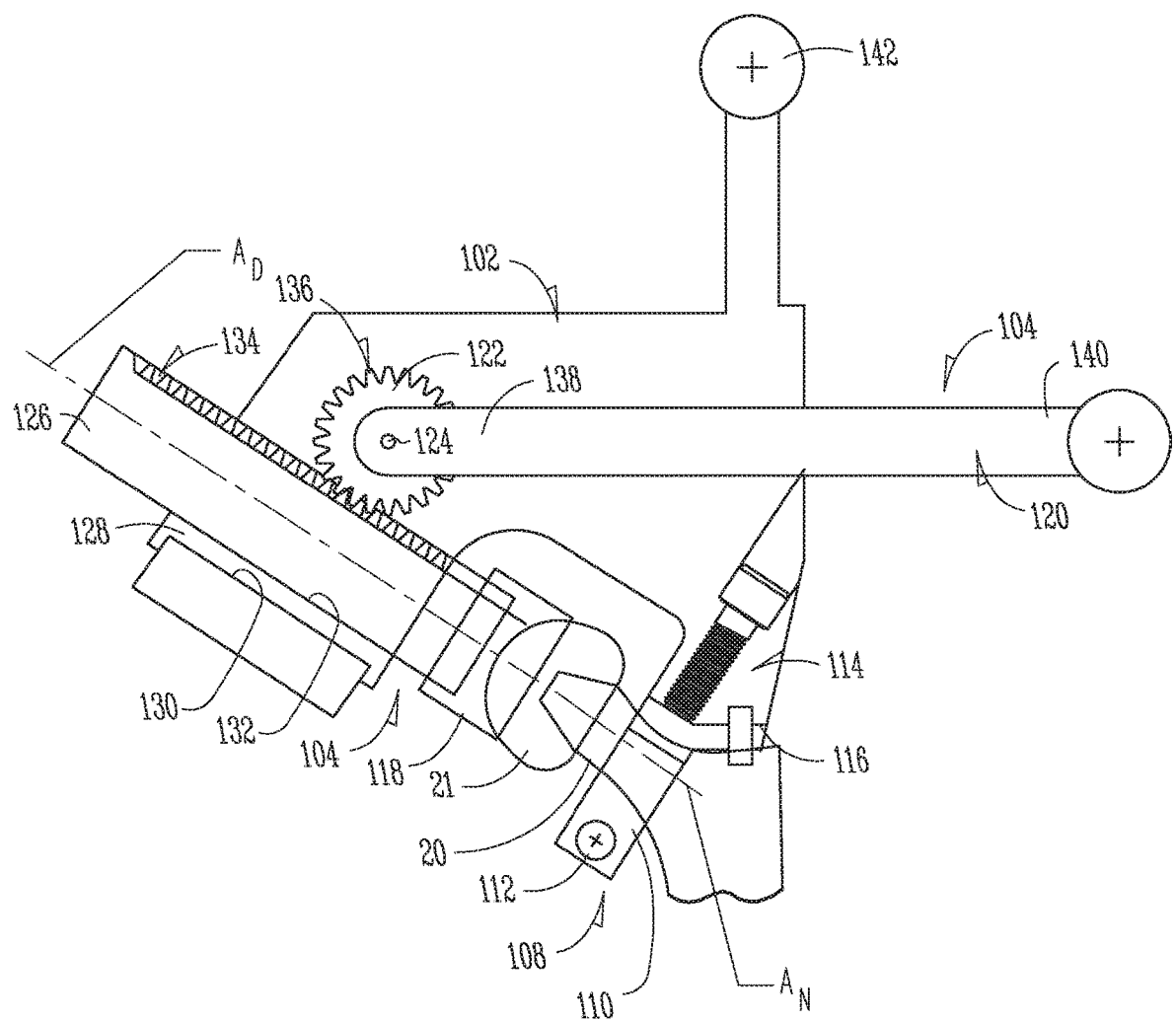
FIG. 4 is a side schematic view of a femoral head press having a frame that attaches to a stem neck and a mechanical press comprising a geared ram.

FIG. 4 is a side schematic view of femoral head press 100 having frame 102 that attaches to stem neck 20 and mechanical press 104 comprising geared ram 106. Femoral head press 100 can also include clamp mechanism 108. Prosthetic stem 12 includes shank 19 (FIG. 1A), neck 20 and head 21. Shank 19 of stem 12 can be inserted into cancellous bone of a femur (not shown) in a manner so that neck 20 extends from a resected proximal end of the femur wherein the natural or anatomic femoral head is removed. Neck 20 can extend from shank 19 along neck axis $A_N$.

Frame 102 can be of similar construction as that of frame 14 of FIG. 1A. Likewise, clamp mechanism 108 can include collar 110 that operates in a similar fashion as that of clamp mechanism 18 and collar 32 of FIG. 1A. For example, collar 110 can include locking device 112, tensioning device 114 and insert 116. Further description is not provided here except to say that collar 110 can align neck axis $A_N$ with drive axis $A_D$ as has been previously described. Head 21 can be attached to cup 118. Cup 118 can be of similar construction as cup 44 of FIG. 1A.

Geared ram 106 can include lever arm 120, gear 122, pin 124, shaft 126, and sleeve 128. Sleeve 128 can be inserted into bore 130 in frame 102, and shaft 126 can be inserted into channel 132 in sleeve 128. Sleeve 128 can act as a bushing or bearing surface to facilitate sliding of shaft 126 within frame 102. Shaft 126 can include gear teeth 134 that are sized and shaped to mesh with gear teeth 136 on gear 122. First end 138 of arm 120 and gear 122 can be pinned to frame 102 via pin 124. First end 138 and gear 122 can be attached so that gear 122 can rotate about pin 124 while arm 120 can simultaneously pivot at pin 124. Gear 122 and first end 138 can be immobilized with reference to frame 102 via pin 124. In other words, gear teeth 136 can orbit or rotate around pin 124 as second end 140 of arm 120 is moved about an arc. When arm 120 is rotated up (with reference to the orientation of FIG. 4), gear 122 can rotate counterclockwise to push shaft 126 downward toward neck 20 through engagement of gear teeth 136 with gear teeth 134. When arm 120 is rotated down (with reference to the orientation of FIG. 4), gear 122 rotates clockwise to push shaft 126 upward away from neck 20 through engagement of tear teeth 136 with gear teeth 134. Frame 102 can include a slot (not shown) that receives arm 120 and that allows arm 120 to rotate about pin 124. Frame 102 can include handle 142 that facilitates grasping and balancing of femoral head press 100 and actuation of lever arm 120.

Figure 5:
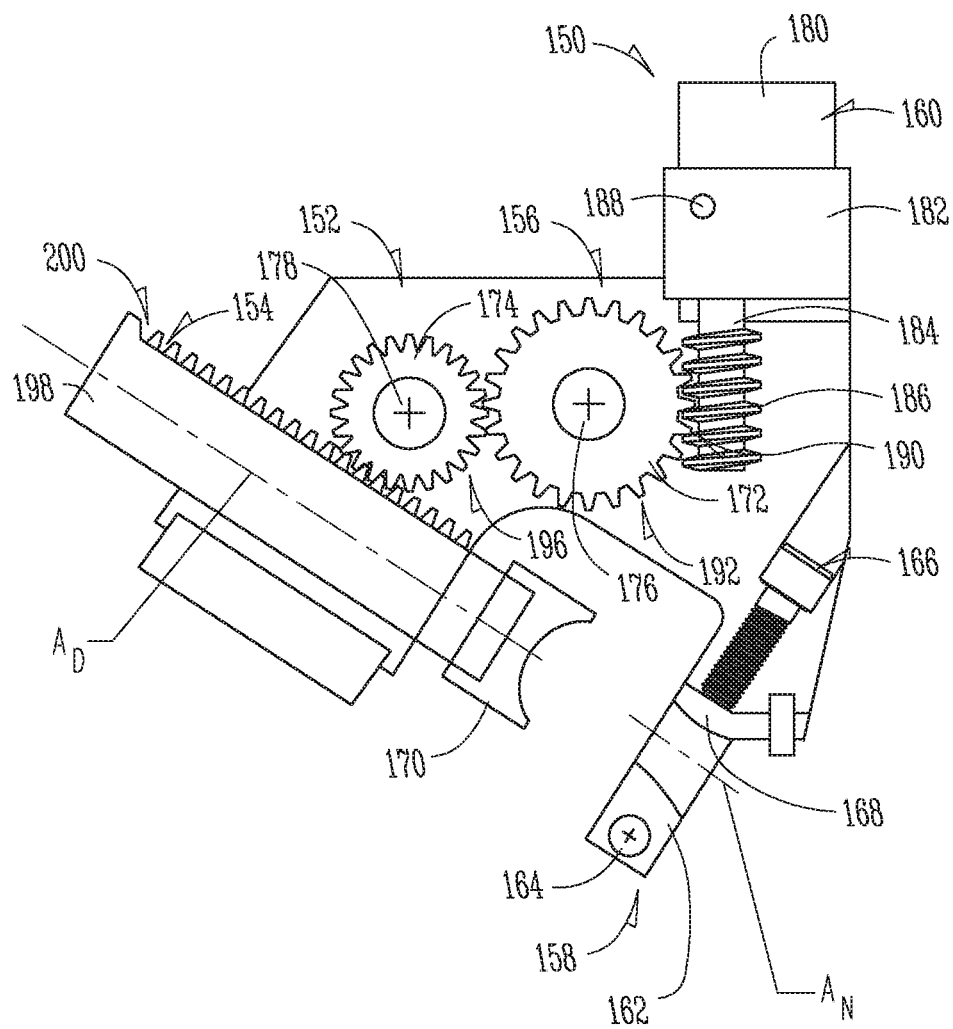
FIG. 5 is a side schematic view of a femoral head press having a frame that attaches to a stem neck and a mechanical press comprising a motor-driven geared ram system.

FIG. 5 is a side schematic view of femoral head press 150 having frame 152 that attaches to stem neck 20 (FIG. 4) and mechanical press 154 comprising motor-driven geared ram system 156. Femoral head press 150 can also include clamp mechanism 158 and motor 160.

Frame 152 can be of similar construction as that of frame 102 of FIG. 4. Likewise, clamp mechanism 158 can include collar 162 that operates in a similar fashion as that of clamp mechanism 108 and collar 110 of FIG. 4. For example, collar 162 can include locking device 164, tensioning device 166 and insert 168. Further description is not provided here except to say that collar 162 aligns neck axis $A_N$ with drive axis $A_D$ as has been previously described. Head 21 (FIG. 4) can be attached to cup 170. Cup 170 can be of similar construction as cup 118 of FIG. 4.

Motor-driven geared ram system 156 can include first gear 172 and second gear 174, which can be mounted on pins 176 and 178, respectively. As such, gears 172 and 174 are stationary with respect to frame 152, but are free to rotate about pins 176 ad 178.

Motor 160 can include housing 180, which can be coupled to frame 150 via mounting bracket 182. Mounting bracket 182 can be connected to housing 180 and frame 150 by any suitable means, such as fasteners, welding or the like. Motor 160 can also include drive shaft 184, which can be connected to worm gear 186 via any suitable method. For example, drive shaft 184 can be directly welded to worm gear 186 as shown in FIG. 5. In other examples, drive shaft 184 can coupled to worm gear 186 via a socket (not shown) or some other mechanical interaction. Motor 160 can include activation button 188 that can be depressed to commence rotation of drive shaft 184. Motor 160 can be activated by any suitable power source. For example, motor 160 can be an electric motor or a pneumatic motor. Motor 160 can be powered by an internal power source, such as a battery, or an external power source, such as a power cord connected to an electrical outlet or an air hose connected to a source of compressed air.

Operation of motor 160, in an example, can allow for rotation of drive shaft 184 in forward and reverse directions. In a forward direction, drive shaft 184 can rotate to cause clockwise rotation of first gear 172 via engagement of gear teeth 190 on worm gear 186 with gear teeth 192 on first gear 172. Clockwise rotation of first gear 172 can cause counterclockwise rotation of second gear 174 via engagement of gear teeth 192 with gear teeth 196 of second gear 174. Counterclockwise rotation of second gear 174 can cause downward (with respect to the orientation of FIG. 5) movement of shaft 198 of mechanical press 154 via engagement of gear teeth 196 with gear teeth 200 of shaft 198. Thus, cup 170 can be advanced toward collar 158 with drive axis $A_D$ aligned with neck axis $A_N$.

In a reverse direction, drive shaft 184 can rotate to cause counterclockwise rotation of first gear 172 and clockwise rotation of second gear 174, which can cause upward (with respect to the orientation of FIG. 5) movement of shaft 198 of mechanical press 154 to withdraw cup 170 away from collar 158.

Motor 160 can allow a surgeon or operator of femoral head press 150 to automatically and precisely control placement of head 21 (FIG. 1A). Thus, the surgeon can concentrate on monitoring engagement of head 21 with neck 20 and the rest of the surgical procedure, rather than being distracted by operation of mechanical press 154.

Any of the femoral head presses described herein are beneficial in achieving proper alignment and assembly between head 21 and neck 20. Without proper alignment and assembly, the junction between head 21 and neck 20 can experience fretting corrosion in vivo which may produce deleterious products that result in pain, adverse tissue reactions, pseudo tumors, etc. Several factors, including impaction load, misalignment, materials combinations, tolerances, head diameter have been postulated to affect the extent of the fretting corrosion. The femoral head presses described herein can allow for the seating of head 21 onto neck 20 in a consistent and reproducible manner to reduce or eliminate surgeon-to-surgeon variability, which subsequently can reduce or eliminate fretting corrosion. The femoral head presses described herein can allow femoral head 21 to fully seat on neck 20 as intended, e.g. wherein neck axis $A_N$ is aligned with the axis of head 21, and head 21 is pushed onto neck 20 with the proper amount of force, thereby removing the variation that may occur from surgeons using a mallet to seat head 21.

Each of the femoral head presses described herein use a mechanical loading force to seat femoral head 21 uniformly onto neck 20. The femoral head presses can include a machine or device that utilizes a mechanical advantage (e.g., gears, levers, motors, torque transmission, pneumatics), to allow the surgeon to apply the appropriate amount of force, with little effort (e.g. without the need for swinging a hammer or mallet). The device can be repeatedly moved along a single loading or drive axis $A_D$. The femoral head 21 can be attached to the device using a cup that ensures the head axis AH is aligned with the drive axis $A_D$. The device can be attached to prosthetic stem 12 via a frame having a clamp mechanism that ensures the neck axis $A_N$ is aligned with the drive axis $A_D$, thereby ensuring alignment of the neck axis $A_N$ with the head axis AH when femoral head 21 is in the cup. The frame can be used manually or can be used in conjunction with a stand that would allow the surgeon to more easily manipulate the femoral head press with the least effect on the patient.

VARIOUS NOTES & EXAMPLES

Example 1 can include or use subject matter such as a femoral head press that can comprise: a frame having a first end and a second end; a clamp connected to the first end of the frame, the clamp defining a holding plane; a mechanical drive mechanism mounted to the second end of the frame, the mechanical drive mechanism having a drive axis; a ram connected to the second end of the frame; and a femoral head cup connected to the ram; wherein the mechanical drive mechanism is configured to drive the ram along the drive axis substantially perpendicular to the holding plane to advance the femoral head cup toward the clamp.

Example 2 can include, or can optionally be combined with the subject matter of Example 1 to optionally include, a clamp that can include a collar for attaching to a neck of a femoral stem, wherein the clamp is configured to hold a center of the neck at the drive axis.

Example 3 can include, or can optionally be combined with the subject matter of one or any combination of Examples 1 or 2 to optionally include, a clamp that can include an insert for buffering against the collar.

Example 4 can include, or can optionally be combined with the subject matter of one or any combination of Examples 1 through 3 to optionally include an insert that can be made of a resilient material.

Example 5 can include, or can optionally be combined with the subject matter of one or any combination of Examples 1 through 4 to optionally include an insert that cab be captured in the collar.

Example 6 can include, or can optionally be combined with the subject matter of one or any combination of Examples 1 through 5 to optionally include a clamp that can open to accept the insert.

Example 7 can include, or can optionally be combined with the subject matter of one or any combination of Examples 1 through 6 to optionally include a clamp that can include a tensioner that pushes the insert within the holding plane within the collar.

Example 8 can include, or can optionally be combined with the subject matter of one or any combination of Examples 1 through 7 to optionally include a clamp that can include a first fastener for closing the collar.

Example 9 can include, or can optionally be combined with the subject matter of one or any combination of Examples 1 through 8 to optionally include, a frame that can include a balance handle spaced from the mechanical drive mechanism.

Example 10 can include, or can optionally be combined with the subject matter of one or any combination of Examples 1 through 9 to optionally include a femoral head cup that can include fingers.

Example 11 can include, or can optionally be combined with the subject matter of one or any combination of Examples 1 through 10 to optionally include a mechanical drive mechanism that can include a machine that produces a mechanical advantage.

Example 12 can include, or can optionally be combined with the subject matter of one or any combination of Examples 1 through 11 to optionally include a mechanical drive mechanism that can include a motor.

Example 13 can include, or can optionally be combined with the subject matter of one or any combination of Examples 1 through 12 to optionally include a mechanical drive mechanism that can comprise a threaded engagement between the frame and the ram, and the ram further comprises a knob.

Example 14 can include, or can optionally be combined with the subject matter of one or any combination of Examples 1 through 13 to optionally include a mechanical drive mechanism that can comprise: a lever arm having a first end and a second end, the first end coupled to the frame and the second end extending from of the frame; a toothed gear coupled to the first end of the lever arm; and a gear tooth track extending along the ram.

Example 15 can include, or can optionally be combined with the subject matter of one or any combination of Examples 1 through 14 to optionally include, a mechanical drive mechanism that can comprise: a motor having a worm gear; a gear system; and a gear tooth track extending along the ram.

Example 16 can include or use subject matter such as a method for assembling a femoral head to a neck of a femoral stem of a prosthetic device, the method comprising: attaching a clamp of a frame of a femoral head press to a neck of a femoral stem; connecting a femoral head to a cup connected to a ram slidably engaged with the frame; and actuating a mechanical drive mechanism coupled to the frame to advance the ram and the cup toward the neck.

Example 17 can include, or can optionally be combined with the subject matter of Example 16 to optionally include actuating the mechanical drive mechanism that can comprise rotating a threaded ram to advance the ram and the cup toward the neck.

Example 18 can include, or can optionally be combined with the subject matter of one or any combination of Examples 16 or 17 to optionally include actuating the mechanical drive mechanism that can comprise rotating a lever connected to a toothed ram to advance the ram and the cup toward the neck.

Example 19 can include, or can optionally be combined with the subject matter of one or any combination of Examples 16 through 18 to optionally include actuating a motor to operate the mechanical drive mechanism and advance the ram and the cup toward the neck.

Example 20 can include, or can optionally be combined with the subject matter of one or any combination of Examples 16 through 19 to optionally include attaching the clamp of the frame of the femoral head press to the neck of the femoral stem that can comprise positioning an insert within the clamp to align the neck with the ram.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A femoral head press comprising:
a frame having a first end and a second end;

a clamp connected to the first end of the frame, the clamp defining a holding plane and the clamp comprising:
    a collar for attaching to a neck of a femoral stem;
    an insert positioned in the collar for buffering against the collar, wherein the collar is configured to open to accept the insert and wherein the insert comprises:
        a socket configured to mate with the neck of the femoral stem; and
        exterior surfaces configured to mate with the collar, wherein the exterior surfaces comprise:
            a first channel configured to receive a first mating portion of the collar; and
            a second channel configured to receive a second mating portion of the collar; and
    a tensioner including a first fastener extending through the collar configured to displace the insert within the collar along the holding plane;
a mechanical drive mechanism mounted to the second end of the frame, the mechanical drive mechanism having a drive axis, the mechanical drive mechanism further comprising a ram connected to the second end of the frame; and
a femoral head cup connected to the ram;
wherein the mechanical drive mechanism is configured to drive the ram along the drive axis substantially perpendicular to the holding plane to advance the femoral head cup toward the clamp;
wherein the clamp is configured to hold a center of the neck of the femoral stem parallel to the drive axis; and
wherein the tensioner is configured to position the insert such that the center of the neck of the femoral stem aligns with the drive axis.

2. The femoral head press of claim 1, wherein the insert is made of a resilient material.

3. The femoral head press of claim 1, wherein the insert is captured in the collar.

4. The femoral head press of claim 1, wherein:
the clamp includes a second fastener for closing the collar.

5. The femoral head press of claim 4, wherein:
the collar comprises:
    a fixed jaw; and
    a rotatable jaw that is pivotable away from the fixed jaw to allow the collar to open to receive the insert;
wherein the second fastener is configured to extend through the fixed jaw and the rotatable jaw to close the collar; and
wherein the insert includes a split configured to allow the insert to open to receive the neck of the femoral stem.

6. The femoral head press of claim 1, wherein the frame includes a balance handle spaced from the mechanical drive mechanism.

7. The femoral head press of claim 1, wherein the femoral head cup includes fingers.

8. The femoral head press of claim 1, wherein the mechanical drive mechanism includes a machine that produces a mechanical advantage.

9. The femoral head press of claim 1, wherein the mechanical drive mechanism includes a motor.

10. The femoral head press of claim 1, wherein the mechanical drive mechanism comprises a threaded engagement between the frame and the ram, and the ram further comprises a knob.

11. The femoral head press of claim 1, wherein the mechanical drive mechanism comprises:
a lever arm having a first end and a second end, the first end coupled to the frame and the second end extending from the frame;
a toothed gear coupled to the first end of the lever arm; and
a gear tooth track extending along the ram.

12. The femoral head press of claim 1, wherein the mechanical drive mechanism comprises:
a motor having a worm gear;
a gear system; and
a gear tooth track extending along the ram.

13. The femoral head press of claim 1, further comprising:
the femoral stem having the neck; and
a femoral head having a socket configured to mate with the neck of the femoral stem;
wherein the femoral stem is configured to mount in the clamp and the femoral head is configured to mount in the femoral head cup such that the neck of the femoral stem and the socket axially align.

14. The femoral head press of claim 13, wherein the insert comprises:
a socket configured to mate with the neck of the femoral stem; and
exterior surfaces configured to mate with the collar.

15. The femoral head press of claim 1, further comprising a plurality of inserts, each of the plurality of inserts having exterior surfaces that are shaped identically to mate with the collar and sockets having interior surfaces that are shaped differently to mate with different femoral stems.

16. The femoral head press of claim 1, herein the socket comprises:
a curved forward surface; and
a flat rear surface.

17. The femoral head press of claim 1, wherein:
the frame includes a first bore; and
the insert further comprises an extension portion comprising a second bore configured to align with the first bore when the insert is positioned within the collar such that a third fastener can be positioned through the second bore and into the first bore.

18. A femoral head press comprising:
a frame having a first end and a second end;
a clamp connected to the first end of the frame, the clamp defining a holding plane and the clamp comprising:
    an adjustable collar for attaching to a neck of a femoral stem;
    a removable insert positioned in the adjustable collar for buffering against the adjustable collar, the removable insert comprising:
        a socket configured to mate with the neck of the femoral stem; and
        exterior surfaces configured to interlock with the adjustable collar;
a mechanical drive mechanism mounted to the second end of the frame, the mechanical drive mechanism having a drive axis, the mechanical drive mechanism further comprising a ram connected to the second end of the frame; and
a femoral head cup connected to the ram;
wherein the mechanical drive mechanism is configured to drive the ram along the drive axis substantially perpendicular to the holding plane to advance the femoral head cup toward the clamp; and
wherein the insert is one of a plurality of inserts, each of the plurality of inserts having exterior surfaces that are shaped identically to mate with the adjustable collar and sockets having interior surfaces that are shaped differently to mate with different femoral stems.

19. A femoral head press comprising:
a frame having a first end and a second end;

a clamp connected to the first end of the frame, the clamp defining a holding plane and the clamp comprising:
  a collar for attaching to a neck of a femoral stem, the collar comprising:
    a fixed jaw;
    a rotatable jaw that is pivotable away from the fixed jaw to allow the collar to open; and
    a first fastener configured to extend through the fixed jaw and the rotatable jaw to close the collar;
  an insert positioned in the collar for buffering against the collar, wherein the insert includes a split configured to allow the insert to open to accept the neck of the femoral stem; and
  a tensioner including a second fastener extending through the collar configured to displace the insert within the collar along the holding plane;
a mechanical drive mechanism mounted to the second end of the frame, the mechanical drive mechanism having a drive axis, the mechanical drive mechanism further comprising a ram connected to the second end of the frame; and
a femoral head cup connected to the ram;
wherein the mechanical drive mechanism is configured to drive the ram along the drive axis substantially perpendicular to the holding plane to advance the femoral head cup toward the clamp;
wherein the clamp is configured to hold a center of the neck of the femoral stem parallelto the drive axis; and
wherein the tensioner is configured to position the insert such that the center of the neck of the femoral stem aligns with the drive axis.

\* \* \* \* \*

UNITED STATES PATENT AND TRADEMARK OFFICE
CERTIFICATE OF CORRECTION

PATENT NO. : 10,722,383 B2
APPLICATION NO. : 15/592309
DATED : July 28, 2020
INVENTOR(S) : Matthew Steif Page 1 of 1

It is certified that error appears in the above-identified patent and that said Letters Patent is hereby corrected as shown below:

In the Claims

In Column 12, Line 27, in Claim 16, delete "herein" and insert --wherein-- therefor In Column 13, Line 28, in Claim 19, delete "parallelto" and insert --parallel to-- therefor Signed and Sealed this
Fifteenth Day of September, 2020

Andrei Iancu
*Director of the United States Patent and Trademark Office*